(12) United States Patent
Knapp

(10) Patent No.: US 6,284,001 B1
(45) Date of Patent: Sep. 4, 2001

(54) JOINT PROSTHESIS

(76) Inventor: John G. Knapp, 22163 Worchester Dr., Novi, MI (US) 48374

( * ) Notice: Subject to any disclaimer, the term of this patent is extended or adjusted under 35 U.S.C. 154(b) by 0 days.

(21) Appl. No.: 09/492,467

(22) Filed: Jan. 27, 2000

Related U.S. Application Data (62) Division of application No. 09/115,563, filed on Jul. 15, 1998, now Pat. No. 6,099,571.
(60) Provisional application No. 60/052,651, filed on Jul. 16, 1997.

(51) Int. Cl.[7] .................................................. A61F 2/24
(52) U.S. Cl. ........................... 623/21.14; 623/20.15; 623/902; 128/898
(58) Field of Search ........................ 623/21.11, 21.12, 623/21.13, 21.14, 21.15, 21.16, 21.17, 23.4, 20.15, 20.22, 902

(56) References Cited

U.S. PATENT DOCUMENTS

| | | | |
|---|---|---|---|
| 3,805,302 | 4/1974 | Mathys | 623/21 |
| 3,990,118 | 11/1976 | Strickland et al. | 623/21 |
| 4,001,896 * | 1/1977 | Arkangel . | |
| 4,304,011 | 12/1981 | Whelan, III . | |
| 4,352,212 | 10/1982 | Greene et al. | 623/21 |
| 4,759,768 | 7/1988 | Hermann et al. . | |
| 4,944,758 | 7/1990 | Bekki et al. | 623/21 |
| 5,007,933 * | 4/1991 | Sidebotham et al. . | |
| 5,047,059 | 9/1991 | Saffar . | |
| 5,092,896 | 3/1992 | Meuli et al. . | |
| 5,108,443 * | 4/1992 | Branemark | 623/21.15 |
| 5,133,761 | 7/1992 | Krouskop . | |
| 5,147,386 | 9/1992 | Carignan et al. . | |
| 5,171,284 | 12/1992 | Branemark . | |
| 5,258,032 | 11/1993 | Bertin . | |
| 5,290,314 | 3/1994 | Koch et al. . | |
| 5,314,484 | 5/1994 | Huene | 623/21 |
| 5,326,366 | 7/1994 | Pascarella et al. . | |
| 5,336,268 | 8/1994 | Rispeter . | |
| 5,425,777 | 6/1995 | Sarkisian et al. . | |
| 5,522,903 | 6/1996 | Sokolow et al. . | |
| 5,549,681 | 8/1996 | Segmuller et al. . | |
| 5,702,471 | 12/1997 | Grundei et al. . | |
| 5,702,472 * | 12/1997 | Huebner | 623/21.15 |
| 5,984,970 * | 11/1999 | Bramlet . | |

FOREIGN PATENT DOCUMENTS 2651119   3/1991   (FR) .

* cited by examiner

Primary Examiner—Bruce Snow
(74) Attorney, Agent, or Firm—Young & Basile, P.C.

(57) ABSTRACT

A method is provided for implanting a joint prosthesis for a damaged joint, wherein the steps include removing the damaged joint and initially anchoring two stem members into adjacent bones and inserting a temporary occupier at the joint location between the two stem members. The occupier is configured to allow only limited movement of the bones having the stem members. After the area around the occupier has healed, the occupier is removed and a specially configured ball and socket is installed as the joint to allow for incremental adjustments of the ball and socket relative to the two stem members during the installation procedure to simulate the natural bending motion of the joint once healed.

6 Claims, 10 Drawing Sheets

JOINT PROSTHESIS

This is a Divisional Continuing Application of prior application ser. No: 09/115,563 filed Jul. 15, 1998, now U.S. Pat. No. 6,099,571.

FIELD OF THE INVENTION

The invention relates to a joint prosthesis for joint replacement and especially a prosthesis for joint replacement of a finger or toe.

BACKGROUND OF THE INVENTION

Surgically implantable prosthetic replacement devices are known in the art for replacement of joints in the hand or foot as well as elsewhere on the body. Often times these replacement devices are necessary as a result of accidents or diseases such as arthritis. It is desirable to provide a finger or toe prosthesis that imitates the natural range of movement of the replaced finger or toe, that allows slight twisting and lateral movement, but does not allow the joint to move in an unnatural way.

Another concern of a joint prosthesis is the potential failure of the device. Because of the small sized parts used in previous joint prosthesis, and especially when using metal, interfacing the prosthesis with the adjoining bones has been difficult. As a result, fatigue failures have occurred. It is therefore desirable to provide a joint prosthesis made of durable material compatible with human tissue and configured to minimize failure and to allow for replacement of the joint secondary to wear.

SUMMARY OF THE INVENTION

It is the intent of the current invention to address the aforementioned concerns. The prosthesis of the current invention duplicates the natural joint of a finger or a toe. The prosthesis includes a pair of intermedulary implants having a ball and socket combination therebetween. The two intermedulary implants/portions are inserted and anchored into the long shanks of the bone on either side of a faulty joint. Each intermedulary portion has a threaded end which is driven into the adjoining shanks of bone. A specialized driver is provided to screw the threaded ends into the shanks. The specialized driver has a head having a configuration corresponding to the exposed surface of each intermedulary portion to prevent slippage of the driver during insertion or removal of the implant. The bone and tissue surrounding the intermedulary implants may be allowed to heal within the patient with a temporary occupier filling the void of the faulty joint before insertion of the ball and socket configuration. The occupier may also provides a passive exerciser during the healing process to control movement of the surrounding muscles to prevent atrophy. Once the healing process is complete, the occupier is removed and the ball and socket configuration is then inserted to provide the necessary movement for the joint.

The socket has a generally hollow spherical configuration having a surface portion that corresponds and complements the exposed surface area of the intermedulary portions. The complementary surfaces provide a means for the surgeon or physician to incrementally adjust the socket relative to the intermedulary portion during the surgical installation of the ball and socket to provide correct relative positioning of the socket so that natural movement of the joint is realized. Once the socket is aligned to the intermedulary portion, a retaining screw secures the socket to the first intermedulary portion.

The socket has an open slot through the wall of the spherical body for access into the hollow interior by the ball member. The ball member is configured to enter the hollow interior through the slot in one direction and rotate within the hollow interior to confine the ball member therein. Once the ball member is captured within the hollow interior of the socket, another retaining screw secures the ball member to the second intermedulary implant. The ball member then has pivotal movement within the socket so that the second intermedulary implant pivots relative to the first intermedulary implant. The socket and ball member combination also includes a limiting means to limit the movement of the joint prosthesis to the natural movement of a finger or toe.

BRIEF DESCRIPTION OF THE DRAWINGS

The description herein makes reference to the accompanying drawings wherein like reference numerals refer to like parts throughout the several views, and wherein:

FIG. 6a is a side sectional view of a socket for the joint prosthesis of the present invention;

FIG. 6b is a sectional view taken along lines 6b—6b of FIG. 6a;

FIG. 6c is a sectional view taken along lines 6c—6c of FIG. 6b;

FIG. 6d is a sectional view taken along lines 6d—6d of FIG. 6a;

FIG. 7b is a sectional view taken along lines 7b—7b of FIG. 7a;

FIG. 7c is a sectional view taken along lines 7c—7c of FIG. 7a;

DESCRIPTION OF THE PREFERRED AND ALTERNATIVE EMBODIMENTS

The prosthesis of the current invention duplicates the natural joint of a finger or toe. Looking first at FIGS. 1 through 4 and FIG. 25, the prosthesis 5 includes a pair of intermedulary implants 10 and 10a, a socket 12, a ball 14 within the socket 12, and a pair of retaining screws 16 and 16b. The intermedulary implant 10 indicates the proximal end of the joint, that is, the end closest to the wrist or ankle. The intermedulary implant 10a indicates the distal end of the joint, which is closest to the tip of the finger or toe.

Figures 1, 3:
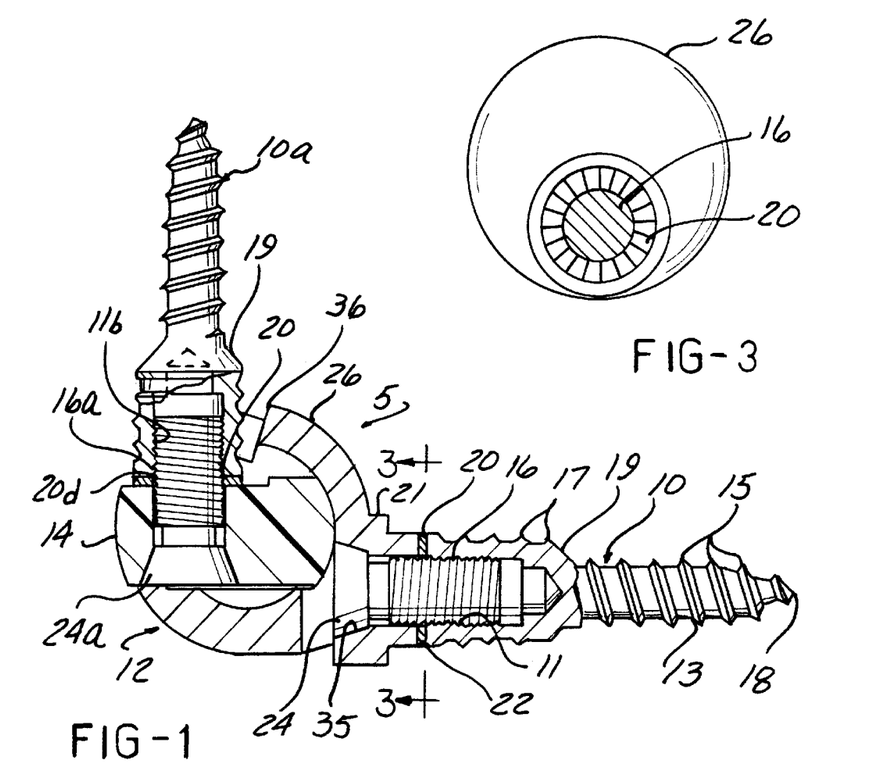
FIG. 1 is a side elevational view of a first embodiment of the joint prosthesis.
FIG. 3 is a sectional view taken along lines 3—3 of FIG. 1.
Figure 5A:
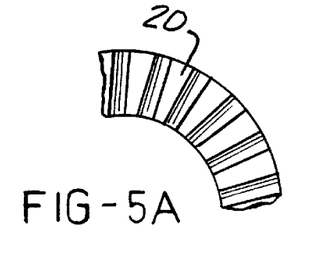
FIG. 5a is a top plan view of a portion of a splined surface of the intermedulary implant.
Figure 5B:
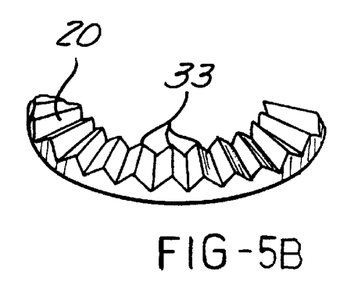
FIG. 5b is a perspective view of a portion of the splined surface.
Figures 6A, 6B, 6C, 6D:
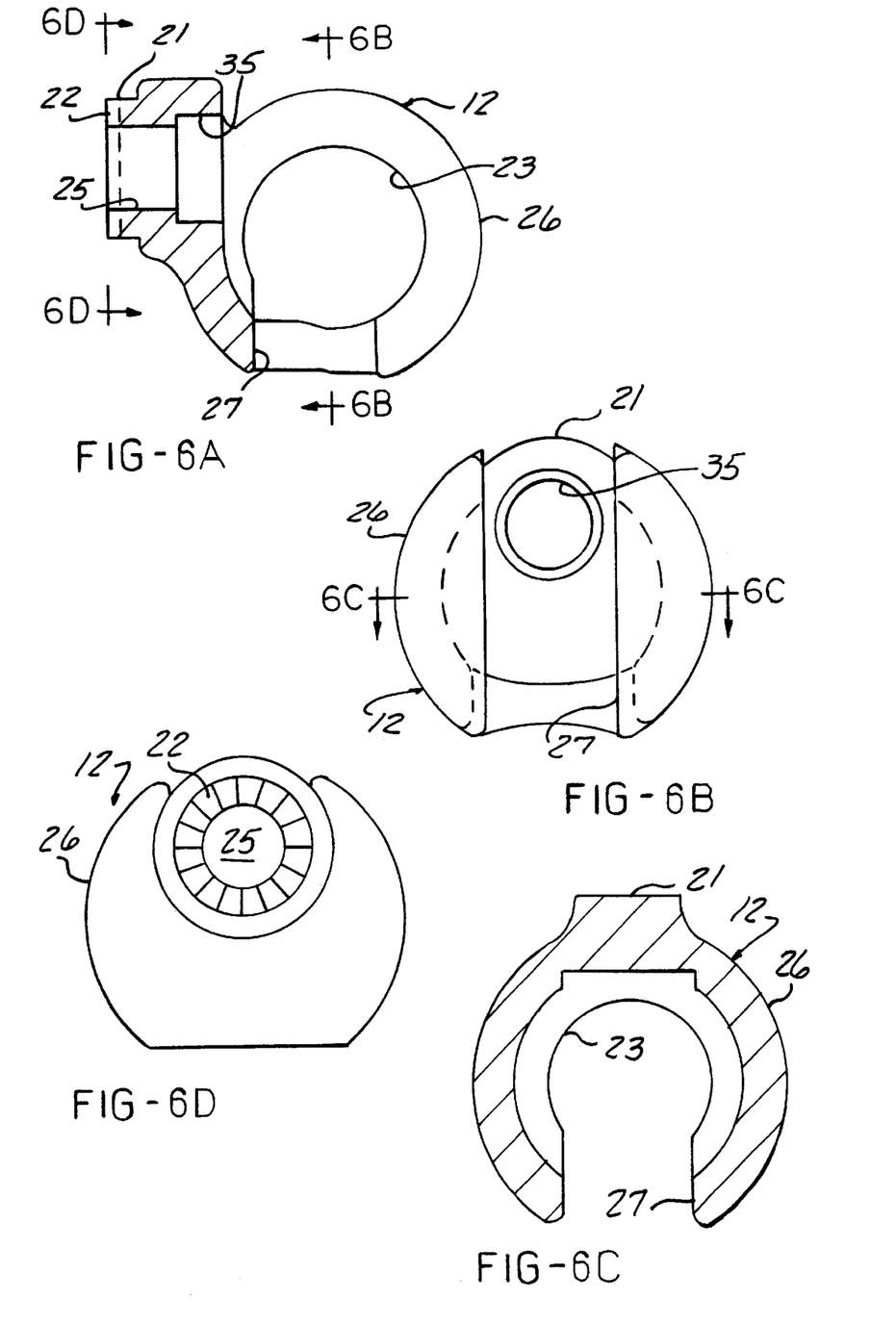

In the first embodiment the intermedulary implant 10 in FIGS. 2 and 2a has a threaded, pointed or tapered end 18 and an opposing end 20 or 20a having a threaded aperture 11 therein for later insertion of one of the retaining screws 16 or 16a. The opposing end surface 20 has a ratcheted or splined outer or facing surface having teeth 33 evenly spaced around the periphery of aperture 11. Partial end and perspective views of the splined surface 20 are shown in FIGS. 5a and 5b. The outer surface 13 of the intermedulary implant 10 may have threads 15 along its entire axial length or partially threaded with circumferential ratchets 17 extending another portion. In FIG. 1, an outwardly tapered surface 19 separates the threaded 15 portion from ratcheted portion 17 to expand the diameter of the intermedulary implant 10 adjacent to the splined surface 20 for receiving a retaining screw 16 therein. As will be described further, the ball or socket will have a complementary surface with the intermedulary implant.

Figures 2, 2A:
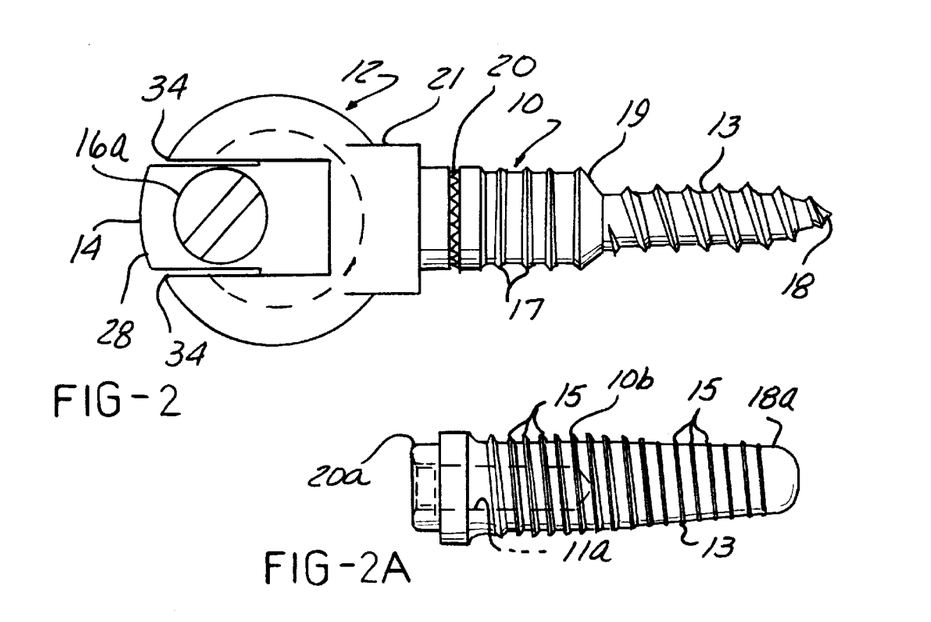
FIG. 2 is a top view of the joint prosthesis.
FIG. 2a is a side elevational view of an alternate intermedulary implant.
Figure 4:
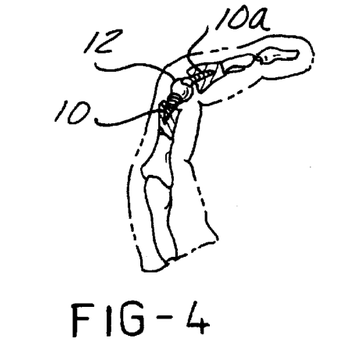
FIG. 4 is a perspective view of the joint prosthesis of the current invention in a finger.

An alternative intermedulary implant 10b is shown in FIG. 2a having a tapered and rounded end 18a. This implant is commercially available and manufactured by Steri-Oss, a Bausch & Lomb Company in California. The opposing end 20a of implant l0b includes a flat horizontal surface having a hexagonal perimeter rather than the splined surface 20. A threaded aperture 11a is located through the hexagonal shaped end 20a and terminating approximately at half the axial length of the implant 10b. The configuration of the implant shown in FIG. 2a may replace either intermedulary implant 10 and 10a shown in FIG. 1. The ball or socket will have a complementary surface to abut the hexagonal flat surface of the intermedulary implant.

The geometry and dimensions of the intermedulary implants 10a, 10b will depend upon the application as well as the patient's physical characteristics. The variables in the geometry of the intermedulary implant includes length, diameter, and thread pitch. A second or distal intermedulary implant is shown at element 10a. This corresponding intermedulary implant 10a may have the exact or different dimensions and configuration of intermedulary implant 10 or 10b. The distal intermedulary implant 10a may have the spline or hexagonal end or other configurations as disclosed hereinafter. Further, it is understood that any configuration disclosed for the proximal intermedulary implant 10 may be used for the distal intermedulary implant 10a. The intermedulary implant is preferably made of a Titanium metal material.

The joint prosthesis 5 also includes a ball 14 and socket 12 combination to connect the two intermedulary implants 10 and 10a and to provide the bending movement of the finger or toe. The socket 12 is shown in FIG. 6a–6d having an essentially spherical configuration having a hollow interior 23 and an extended portion 21 that faces the proximal intermedulary implant 10. The socket is preferably made of a Titanium material. The spherical body 26 has a through access port or slot 27 to the interior 23 of the socket for insertion of the ball 14 which will be discussed further. The extended portion 21 has an end mating surface 22 which corresponds to the end surface 20 of proximal intermedulary implant 10 or 10b. Therefore, in one instance, the end mating surface 22 of socket 12 would have a splined surface to matingly correspond with the splined surface 20 of intermedulary implant 10 as shown in FIGS. 1 and 2. In another instance, the end mating surface 22 may have a flat face, hexagonal shaped end to matingly correspond with hexagonal shaped end 20a in FIG. 2a. Other embodiments of corresponding surfaces will be discussed further. The splined surfaces 20 for connection between the intermedulary implant and socket provides the surgeon or physician incremental movement of the socket 12 relative to the intermedulary implant 10 without slippage when positioning the socket 12 onto the intermedulary implant 10 for correct relative positioning of the socket 12. The hexagonal shaped end 20a provides six incremental positions to place the socket 12 onto intermedulary implant 10.

A through threaded aperture 25 extends from the end mating surface 22 in extended portion 21 to the hollow interior 23 of the socket 12. Once the correct positioning of the intermedulary implant 10 to the socket 12 is achieved, a retaining screw 16 is inserted into the through aperture 25 of the extended portion 21 of socket 14 so that the head 24 of retaining screw 16 is located in an expanded channel 35 and the shank of the screw 16a extends into threaded aperture 11 or 11a of the intermedulary implant 10 to hold and secure the proximal intermedulary implant 10 and socket 12 in a fixed and stationary manner relative to each other. The retaining screw 16 can be a tapered screw for metal or ceramic material or a large head screw for plastic material.

Figure 7A:
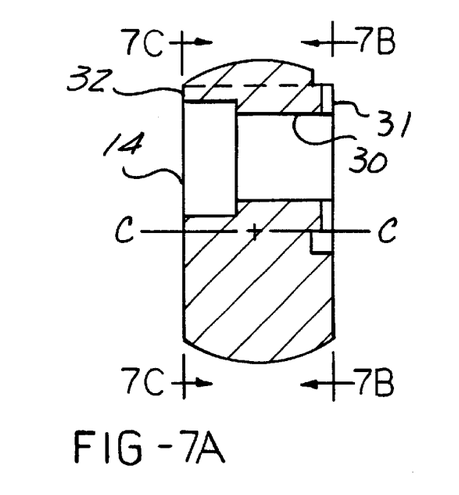
FIG. 7a is a side sectional view of a ball for the joint prosthesis of the present invention.
Figure 7B:
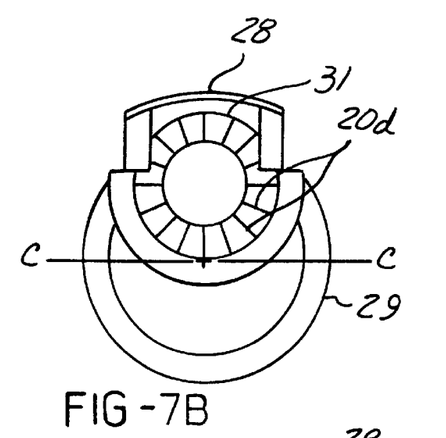
Figure 7C:
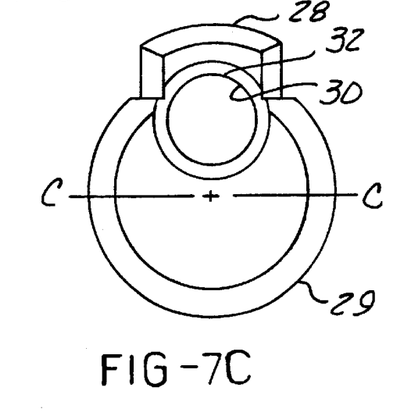

Once the first screw 16 is inserted to hold the socket 12 to the proximal intermedulary implant 10 the ball 14 is inserted into the through access port 27 of the socket 12. The ball is preferably made of a plastic material such as Delrin™. The ball 14 is shown in FIGS. 7a–7c and has the configuration of a spherical ball with two parallel sides sheared off. An arcuate tab 28 extends above the circular portion 29 of ball 14. A through aperture 30 is located between the center line C of ball 14 and the arcuate tab 28. Surrounding a first end 31 of aperture 30 is a circumferential splined surface 20*d*, a flat face hexagonal shaped end, or other configured surface disclosed herein to correspond to the splined surface, hexagonal shaped end, or other shaped surface disclosed herein of the intermedulary implant 11*a*. The other end 32 of aperture 30 has a greater diameter than the first end 31 of the aperture and a depth to receive the head 24 of another retaining screw 16*a* as discussed hereinafter.

Figure 8A:
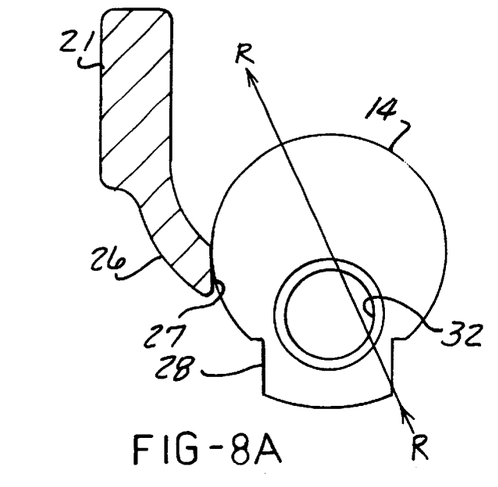
FIGS. 8a–8f therein show the steps for inserting and positioning and securing the ball into the socket.
Figure 8B:
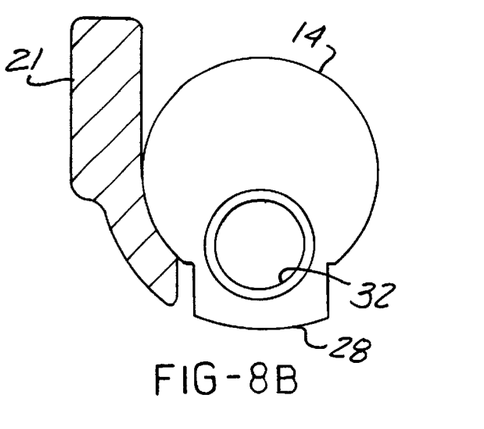
Figure 8C:
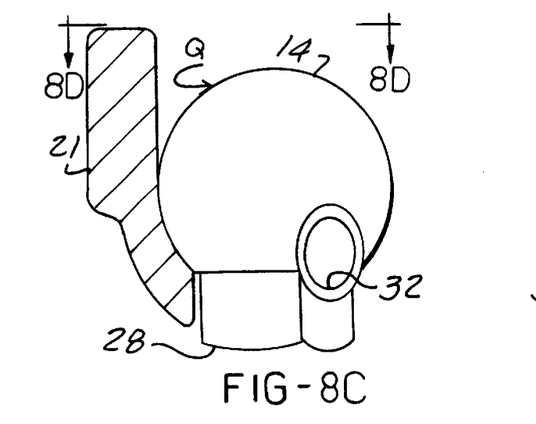
Figure 8D:
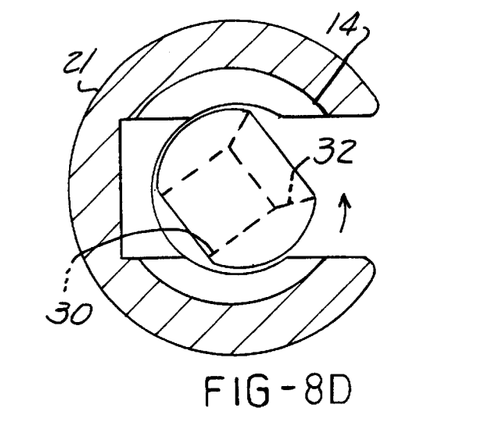
Figure 8E:
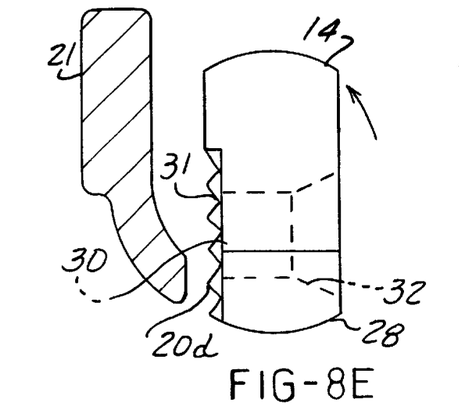
Figure 8F:
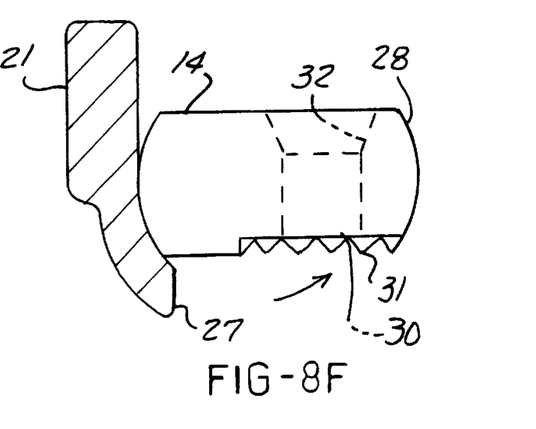

The ball 14 is inserted into the hollow interior 23 of the socket 12 through access port 27 such that the sheared ends fit within the port 27 of the socket 12. The ball 14 is then turned to lock itself within the socket 12. FIGS. 8*a*–8*f* shows the series of maneuvers to insert the ball 14 into socket 12 and to secure it therein. The ball 14 enters socket 12 through access port 27 in an angular direction as designated by arrows R in FIG. 8*a* so that arcuate tab 28 fills the access port 27. When the ball 14 is positioned as shown in FIG. 8*b*, the ball is rotated counterclockwise as designated by arrow Q in FIG. 8*c*. FIG. 8*d* shows that the ball 14 is rotated 180° to reverse the directions of first end 31 and second end 32 of aperture 30 so that the ball 14 is shown as in FIG. 8*e*. The ball 14 is then rotated 90° as shown in FIG. 8*f* which essentially secures the ball within the interior 23 of socket 12.

Once the ball 14 is locked into the socket 12, the other retaining screw 16*a* is inserted through apertures 30 in the ball 14 so that the screw head 24*a* is positioned in end 32, and aperture 11*b* of the second intermedulary implant 10*a*, and tightens the ball 14 to the intermedulary portion 10*a*. The meeting surface 20*d* of end 31 of the ball 14 will have a complementary 20*d* surface to surface 20 of intermedulary implant 10*a*. If the readily available hexagonal shaped ends are used, the surfaces may be adjusted in six increments of 60° before the ball 14 is secured to distal intermedulary implant 10*a*. If splined surfaces are used the degree of adjustability is greater. In either case, the ball 14 and second intermedulary implant 10*a* are secured together to allow limited movement within socket 12.

Figure 9:
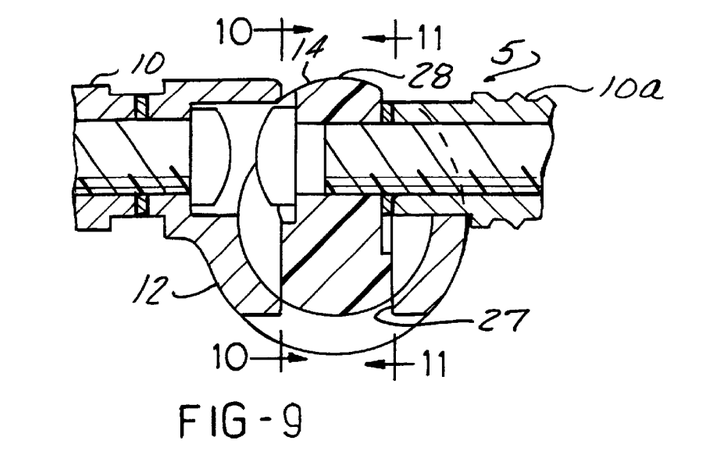
FIG. 9 is a partial side sectional view of the joint prosthesis in a straight position.
Figure 10:
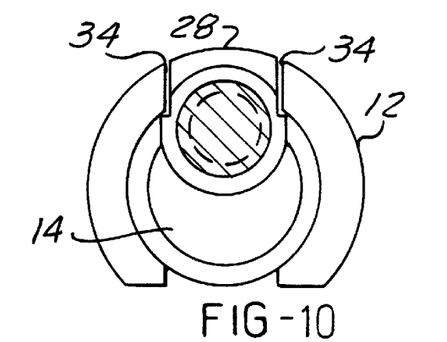
FIG. 10 is a sectional view taken along lines 10—10 of FIG. 9.
Figure 11:
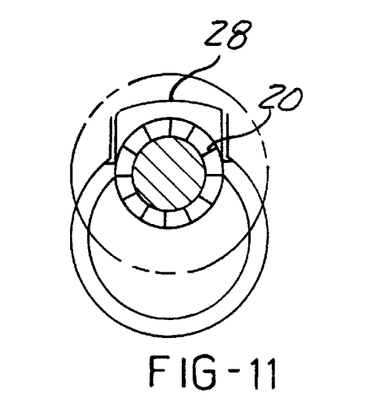
FIG. 11 is a sectional view taken along lines 11—11 of FIG. 9.
Figure 12:
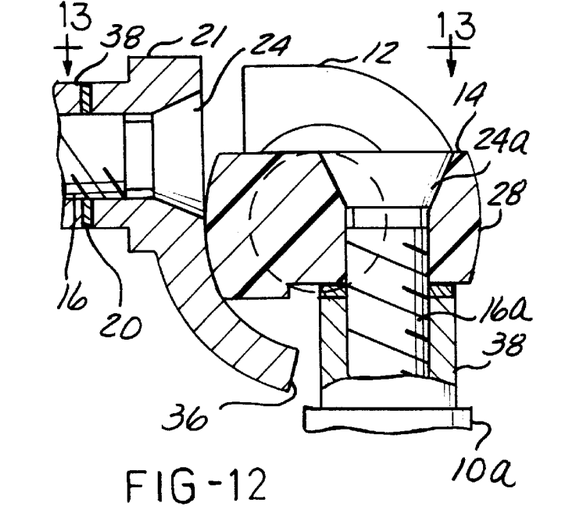
FIG. 12 is a partial side sectional view of the joint prosthesis having a 90° bend.
Figure 13:
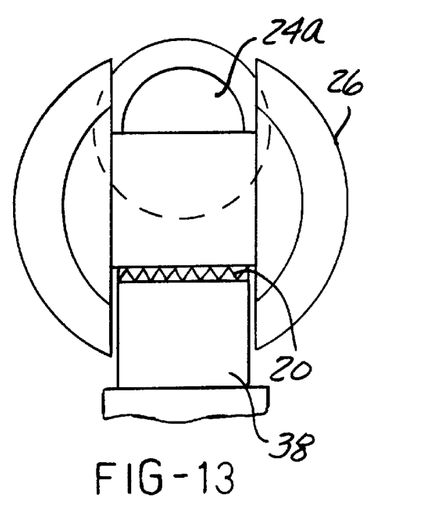
FIG. 13 is a sectional view taken along lines 13—13 of FIG. 12.
Figure 14:
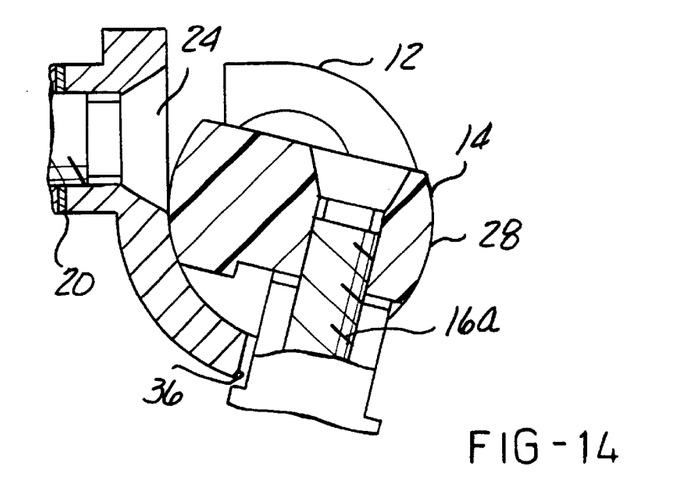
FIG. 14 is a side elevation view of the joint prosthesis when the joint has a bend greater than 90°.

FIGS. 9–14 are views of the assembled joint prosthesis 5 in various positions to show other features of the invention. The arcuate extending tab 28 on the ball 14 is used as a guidance means for the ball 14 and allows pivotal movement of the ball 14 within the access port 27 of socket 12. The ball and socket configuration with the tab 28 allows very limited lateral motion or side to side motion of the joint for the finger or toe. Lateral motion is limited by the gap defined by the space between the stop portions 34 (the peripheral edges of access port 27) and the arcuate tab 28 (see FIGS. 2 and 10). FIGS. 9, 10 and 11 show the prosthesis when the finger (or toe) is in the extended or straight position. FIGS. 1 and 12 shows the ball 14 and socket 12 at a 90° bend. In FIGS. 1 and 12 there is also shown a pivotal stop 36 defined by the opposing edges of slot 27 to prevent overbending of the prosthesis to simulate the natural bending motion of the finger or toe. FIG. 14 shows the ball 14 and socket 12 at a bend greater than 90°.

The geometry of the intermedulary portion 10 may vary. The application and the size of the patient's digit will determine the length, diameter, the thread pitch, as well as other measurements of the intermedulary portion 10. Further, the application may vary the locations of pivot stop 36 on socket 12 and the gap between stops 34 and arcuate tab 28. The prosthesis 5 may also include a length extension 38 (FIG. 12) which may vary in length to join the intermedulary portion 10 or 10*a* to the ball 14 or socket 12. If a length extension 38 is required for the application, the complementary splined, hexagonal or other disclosed surface will be located on extension 38 to accurately position the corresponding surface of the ball.

Figure 15:
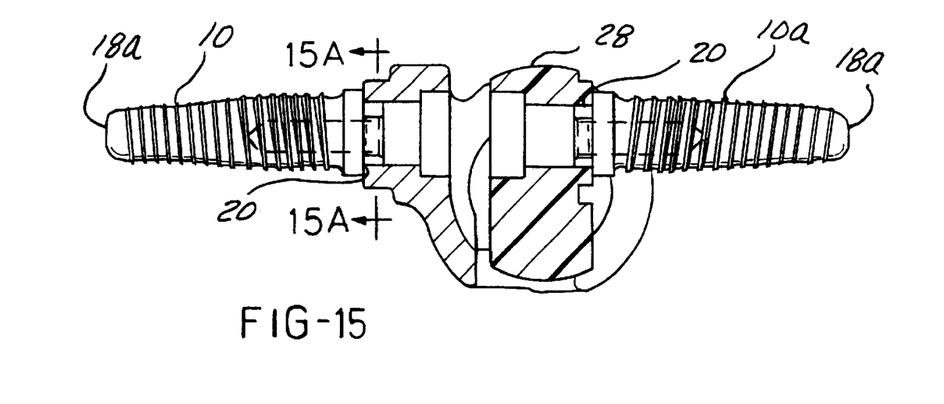
FIG. 15 is a sectional view of the joint prosthesis in an extended position having an external hex end and a tapered opposing end.
Figure 15A:
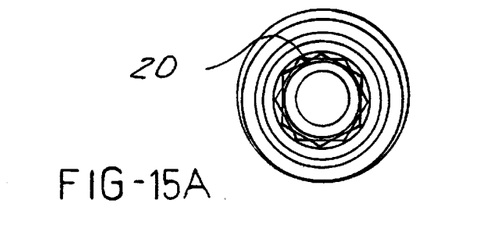
FIG. 15a is a view of the hex end taken along lines 15a—15a of FIG. 15.
Figures 16, 17:
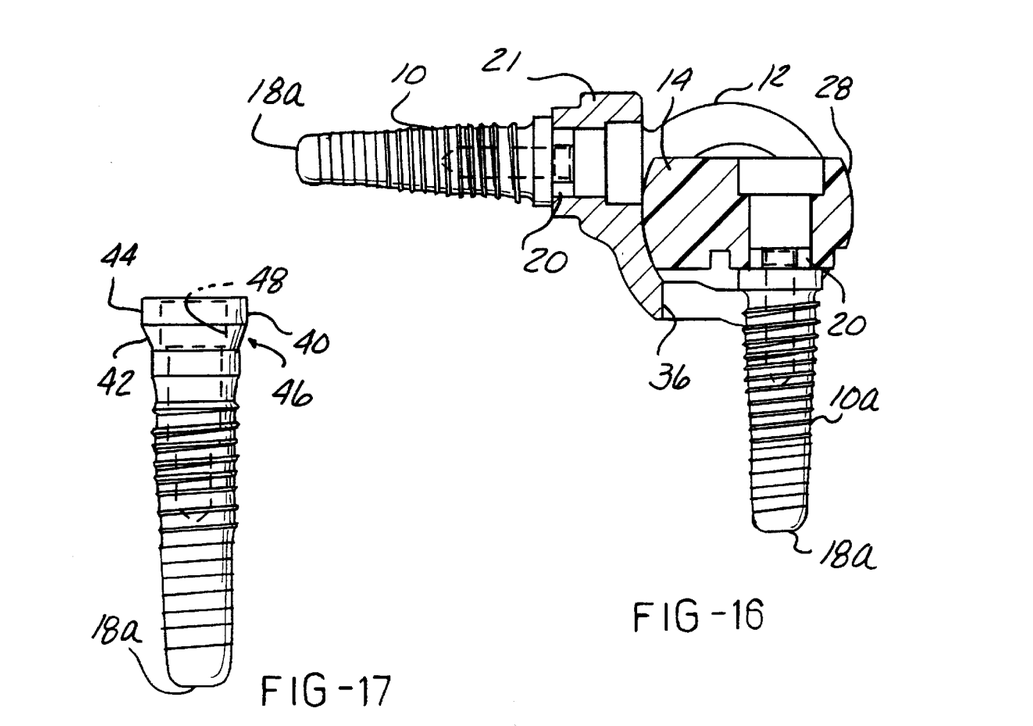
FIG. 16 is a sectional view of the joint prosthesis of FIG. 15 flexed in a 90° position.
FIG. 17 is a sectional view of the intermedulary implant having an external self holding tapered end.

Although the splined surfaces on the intermedulary implants 10, 10*a*, socket 12 and ball 14 provide a wider degree of adjustability for the surgeon than the flat surface hexagonal shape, the hexagonal shape provides manufacturing availability. FIGS. 15, 15*a* and 16 show the use of a hexagonal surface as discussed supra. Other surface configurations, i.e. octagonal, square etc., offering a certain degree of adjustability without slippage may be used.

Figure 18:
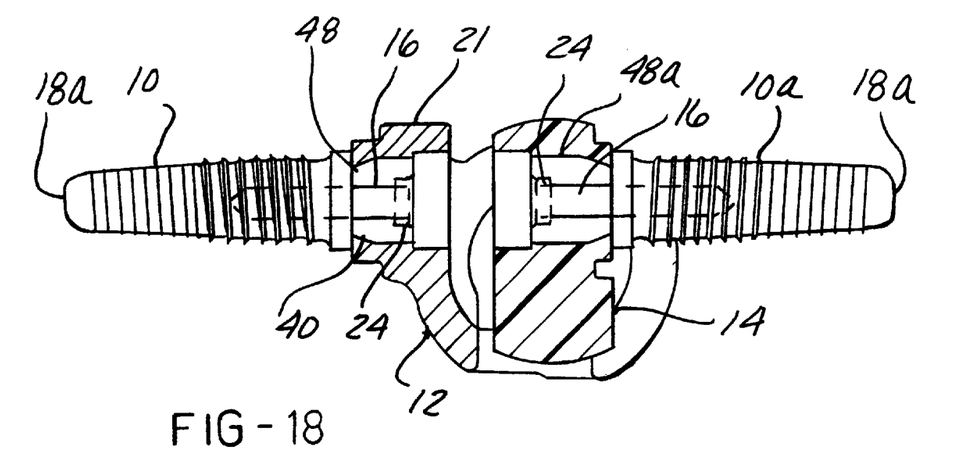
FIG. 18 is a sectional view of a joint prosthesis implementing the intermedulary implants of FIG. 17.
Figure 20:
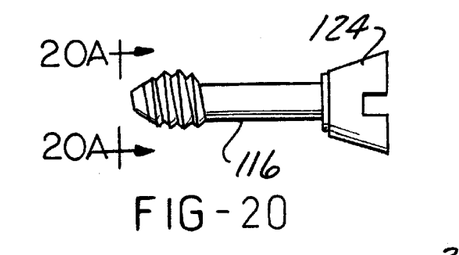
FIG. 20 is an elevational view of a retaining screw for a self holding taper.
Figure 20A:
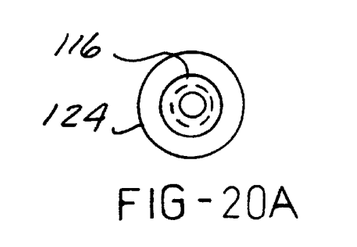
FIG. 20a is a sectional view taken along lines 20a—20a of FIG. 20.

FIGS. 17 and 18 show another surface configuration for the intermedulary implant 10 which allows an unlimited amount of rotating adjustability during the implant procedure. The connection end 40 distal from the tapered surface 18*a* of the intermedulary implant 10, 10*a* has an outwardly tapered portion 42 that straightens to a vertical portion 44 at end 40. The socket 12 and ball 14 will each have a cavity 48 and 48*a* complementary with respect to the configuration of the end 40. The outer surface end 40 is preferably smooth to provide unlimited rotating adjustability. The connection end 40 may also be configured to solely include an outwardly tapered portion 42 the entire length to base 46. FIGS. 20 and 20*a* show modified retaining screw 116 and heads 124 for use with the self holding tapered ends 37.

Figure 19:
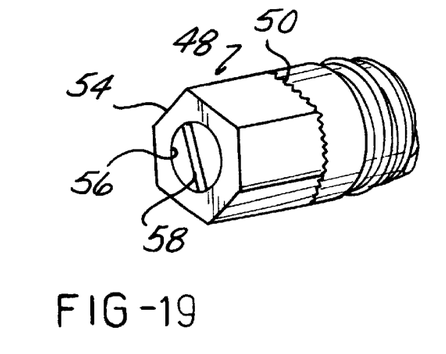
FIG. 19 is a perspective view of a driving means having a splined end.
Figure 21:
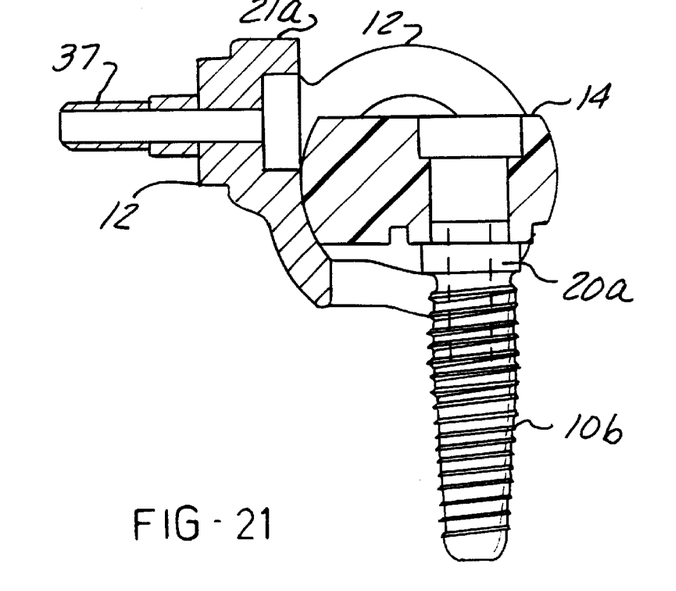
FIG. 21 is a partial sectional view of the socket and intermedulary implant connection having a self holding taper end.

FIG. 21 is a fourth embodiment for complementary surfaces between the intermedulary implant 10, 10*b* and the socket 12. This mating surface configuration is not for use between the ball 14 and intermedulary implant 10*a* because the surface is formed on the extended, portion 21 of the socket 12. FIG. 19 depicts a joint with an external self holding tapered end 37 on the socket 12 for receiving an internally tapered intermedulary portion as shown in FIG. 17. As can be seen, the intermedulary implant 10 can be connected to the extended portion 21 of the socket 12 in FIG. 18, to the ball 14 in FIG. 18, or to the self holding tapered end 21*a* of FIG. 19. If the socket 12 with the self holding tapered end 21*a* is used to connect to one of the intermedulary implant, the ball 14 and corresponding intermedulary implant may have any other complementary surfaces, such as the internal hex end on ball 14 with complementary flat face hex end 20*a* of intermedulary portion 10*b* as shown in FIG. 19. The spline surfaces and the internal self holding tapered surfaces are other alternatives. It is understood that the internal and external self holding tapered configurations offer the greatest amount of adjustability when implanting the prosthesis into the patient. The self holding tapered ends allow the physician to rotate the ball 14 and socket 360°. The external surface also inhibits slippage of the prosthesis 5.

The insertion of the prosthesis of the current invention is preferably performed as a two step procedure. Initially an operation will be conducted to remove the faulty joint. The surgery technique involves an incision on the dorsal surface of the digit over the joint area. The soft tissues are retracted. The desired length of the digit is estimated. The afflicted or diseased joint is resected. Using internally irrigated drill bits, which are commercially available, the intermedulary area of the bone, facing the cut end, is enlarged, shaped and thread tapped to match the intermedulary portion of the implant assembly. The intermedulary portion 10 or 10*a* is threaded into the bone. The appropriately sized occupier joint is selected and attached with screws 16 to the intermedulary portions 10, 10*a*. The tissues are repositioned and the wound is closed. A temporary occupier preferably made of a plastic material, such as Delrin™, will be inserted between the two intermedulary portions 10, 10*a* in place of the removed joint for a period of time while the intermedulary portions 10 and 10a and the adjoining tissue heal.

Figure 22:
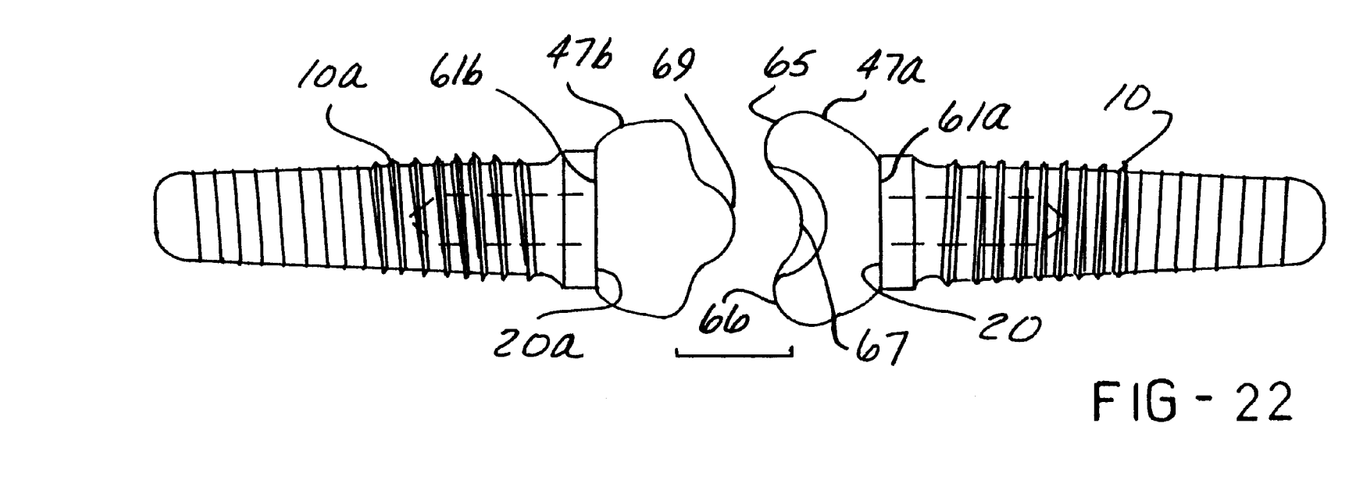
FIG. 22 is a top view of an occupier attached to two intermedulary implants within a joint.
Figure 23:
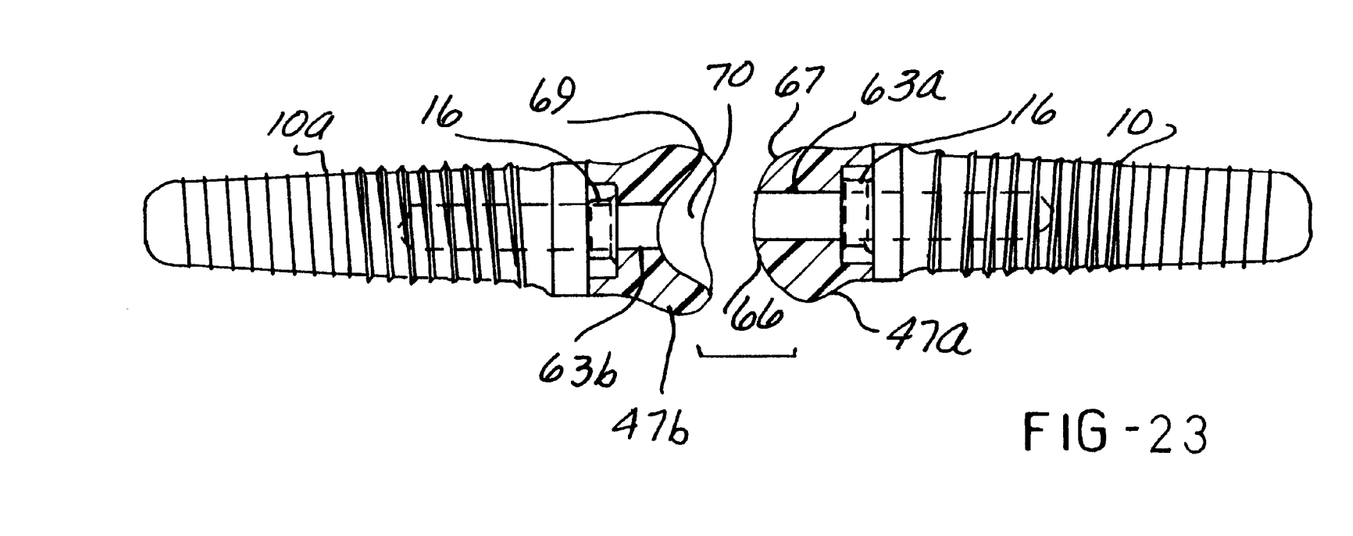
FIG. 23 is a sectional side view of the occupier attached to the two intermedulary implants.
Figure 24:
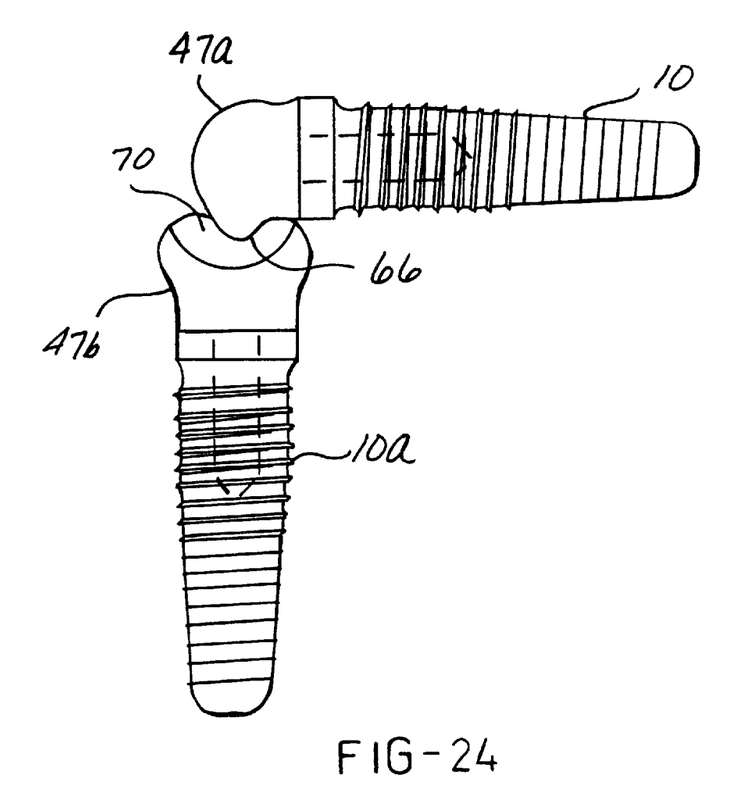
FIG. 24 is a side view of the occupier attached to the two intermedulary implants where the intermedulary implants are connected and articulated at 90 degrees.
Figure 25:
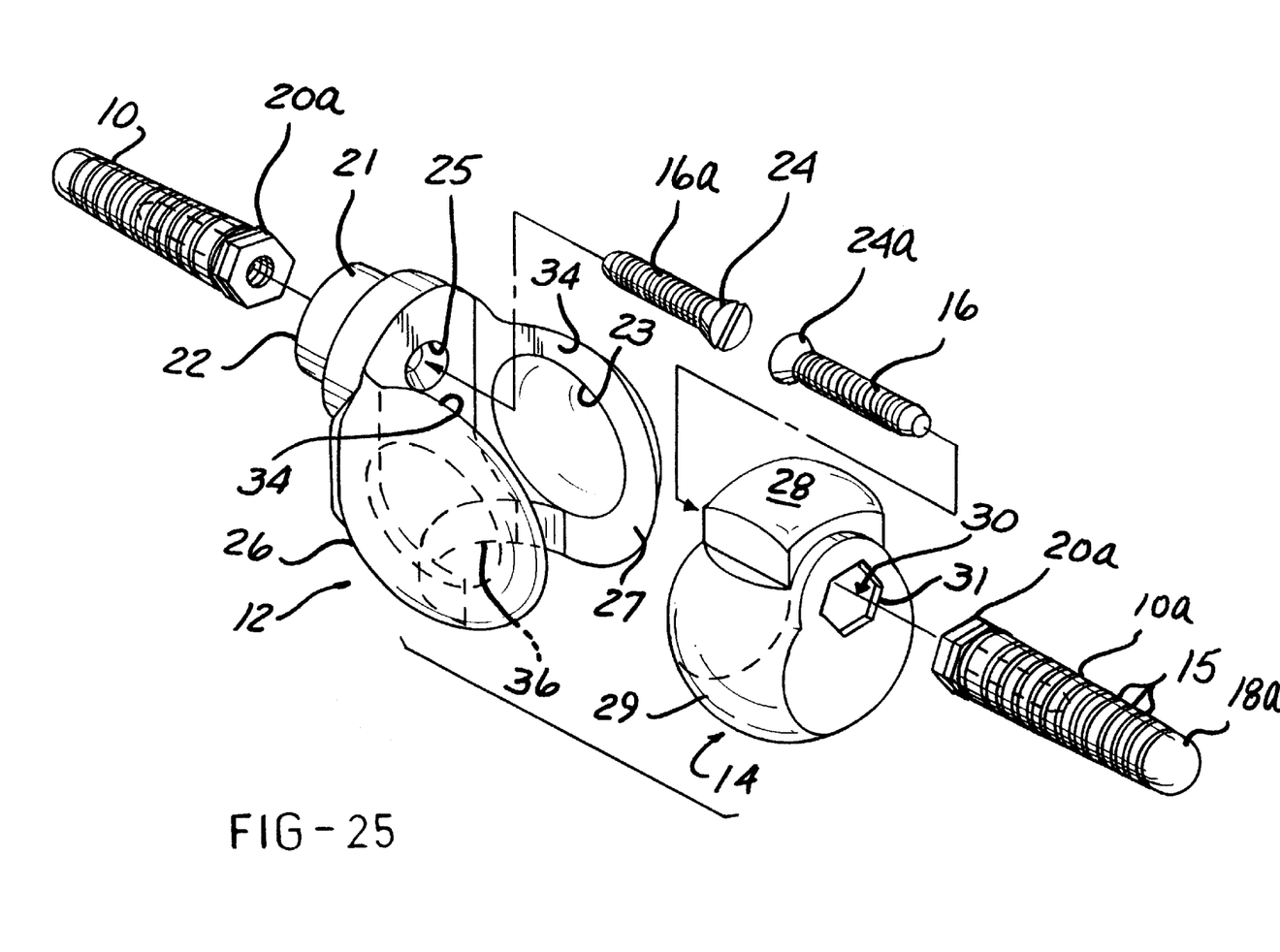
FIG. 25 is an exploded perspective view of the joint prosthesis described in FIGS. 1–3, with the intermedulary implant of FIG. 2A.

The illustrated occupier in FIGS. 22–24 is a two-piece structure having a first piece 47a attached to the proximal intermedulary portion 10 and a second piece 47b attached to the distal intermedulary portion 10a. Each of the occupier pieces 47a, 47b have a flat surface portion 61a, 61b respectively for abutment to respective ends 20, 20a of the corresponding intermedulary portion 10, 10a. Each occupier piece 47a, 47b also has a through aperture 63a, 63b, respectively, as can best be seen in FIG. 23, for receiving the retaining screw 16 to threadably secure the occupier piece 47a, 47b to the corresponding intermedulary portion 10, 10a.

Proximal occupier 47a is configured from the top view in FIG. 22 to have two rounded mound portions 65, 66 with a valley portion 67 therebetween. Distal occupier 47b is configured to complement the proximal occupier 47a so that from the top view (FIG. 22), the distal occupier 47b has a rounded center section 69 which fits within valley portion 67. When the occupier and intermedulary portions are viewed from the side, FIG. 23 and FIG. 24, the distal occupier piece 47b has a valley portion 70 for receiving one of the rounded mound portions 66 of the proximal occupier piece 47a. The valley portion 67 of the proximal occupier piece 47a and the valley portion 70 of the distal occupier piece 47b provide only limited guidance for the corresponding rounded center section 69 and the rounded mound portion 66 when connected, as shown in FIG. 24, to maintain the two occupier pieces together and to allow only limited movement of the finger or toe. Once the intermedulary portions 10, 10a and occupier 47a, 47b are implanted, the incision is closed and the patient's hand or foot is put in a splint or cast. After primary healing, the splint may be removed and the joint may be passively exercised with a commercially available device to prevent atrophy. The passive exerciser gives direction within a fixed range to the movement of the joint. Alternating periods of rest for the joint while in a splint so that the surrounding soft tissue heals with periods of passive exercise is recommended until osseointegration is complete. Another operation will remove the occupier and insert the final ball 14 and socket 12 configuration as described supra.

As an aid to insert the intermedulary implants 10 and 10a into the bone shanks, a driving means is provided to accommodate the various designs of the exposed ends 20, 20a, 40 the intermedulary implants. FIG. 19 shows a driving means 48 for exposed end 20 having a splined surface 50. A hex driver 48 has been devised in which a driver having a hex outer surface 54 has a serrated or splined surface 50 on one side to coincide with the serrated surface 20 of each intermedulary implant 10 and 10a. The hex driver 48 further includes an aperture 56 therethrough. A screw 58 is inserted into the aperture 56 of the hex driver 48 and screwed to drive the intermedulary implant 10 or 10a into the bone shank. Once the intermedulary portion 10 or 10a is inserted, the screw 58 and the hex driver 48 are removed from the intermedulary portions 10, 10a so that the temporary occupier can be installed. If the exposed ends have a hexagonal configuration, a hex socket (not shown) can be used to drive the intermedulary implants 10, 10a into the bone shank.

While the invention has been described in connection with what is presently considered to be the most practical and preferred embodiment, it is to be understood that the invention is not to be limited to the disclosed embodiments but, on the contrary, is intended to cover various modifications and equivalent arrangements included within the spirit and scope of the appended claims, which scope is to be accorded the broadest interpretation so as to encompass all such modifications and equivalent structures as is permitted under the law.

What is claimed is:

1. A method for implanting a joint prosthesis for a damaged joint, the steps comprising:
    removing the damaged joint;
    anchoring a first stem member to a first bone member distal to the joint;
    anchoring a second stem member to a second bone member proximate to the joint;
    providing a temporary occupier to replace the joint, wherein the temporary occupier is configured to allow for only limited movement of the joint which is less than the movement of a natural joint;
    inserting the temporary occupier at the joint location between the first and second stem members;
    connecting the temporary occupier to the first and second stem members while the bones and adjacent tissue heal;
    immobilizing the area around the damaged joint until primary healing is complete;
    then removing the temporary occupier when the bones and adjacent tissue heal; and
    then inserting a permanent joint member in place of the occupier, wherein the permanent joint member is configured to allow the same movement as a natural joint.

2. The method for implanting a joint prosthesis of claim 1 further includes the steps of passively exercising the joint with the temporary occupier to prevent atrophy after the primary healing is complete and before removing the temporary occupier.

3. The method for implanting a joint prosthesis of claim 1 wherein the joint member includes a ball and socket combination.

4. The method for implanting a joint prosthesis of claim 3 further including the step of adjustably aligning the ball and socket to the first and second stem members for providing a natural movement of the joint prosthesis.

5. The method for implanting a joint prosthesis of claim 1, wherein the occupier is a two-piece structure, each piece having an aperture therethrough for receiving a retaining screw for threadably connecting each piece to one of the stem members.

6. The method for implanting a joint prosthesis of claim 1 further including the steps of enlarging, shaping and thread tapping the first and second bone members to match the first and second stem members respectively before anchoring the stem members to the respective bone members.

* * * * *